United States Patent [19]

Louvel

[11] Patent Number: 5,527,814
[45] Date of Patent: Jun. 18, 1996

[54] USE OF 2-AMINO-6-(TRIFLUOROMETHOXY)-BENZOTHIAZOLE FOR OBTAINING A MEDICAMENT FOR THE TREATMENT OF AMYOTROPHIC LATERAL SCLEROSIS

[75] Inventor: Erik Louvel, Manosque, France

[73] Assignee: Rhone Poulenc Rorer S.A., France

[21] Appl. No.: 327,343

[22] Filed: Oct. 21, 1994

Related U.S. Application Data

[63] Continuation of Ser. No. 945,789, Sep. 16, 1992, abandoned.

[30] Foreign Application Priority Data

Mar. 6, 1992 [FR] France .................................. 92 02696

[51] Int. Cl.$^6$ ................................................. A61K 31/425
[52] U.S. Cl. ................................................. 514/367
[58] Field of Search ................................................. 514/367

[56] References Cited

U.S. PATENT DOCUMENTS

| | | | |
|---|---|---|---|
| 4,370,338 | 1/1983 | Mizoule et al. | 424/270 |
| 4,826,860 | 5/1989 | Johnson et al. | 514/367 |
| 4,906,649 | 3/1990 | Blanchard et al. | 514/367 |
| 4,918,090 | 4/1990 | Johnson et al. | 514/367 |
| 4,980,356 | 12/1990 | Audiau et al. | 514/338 |
| 5,026,717 | 6/1991 | Audiau et al. | 514/338 |
| 5,236,940 | 8/1993 | Audiau et al. | 514/367 |

FOREIGN PATENT DOCUMENTS

| | | |
|---|---|---|
| 0282971A3 | 3/1988 | European Pat. Off. |
| WO91/17984 | 11/1991 | WIPO |
| WO91/18892 | 12/1991 | WIPO |

OTHER PUBLICATIONS

Chemical Abstracts 109:31973t, 1988, Stutzmann et al.
Wyngaarden et al. (Editors), *Cecil Textbook of Medicine* (19th Edition), W. B. Saunders Co., Philadelphia, Pa., 1992, pp. 2140–2142.

The Lancet, vol. 341, Jan. 30, 1993, pp. 265–268, "Cell Culture Evidence for Neuronal Degeneration...", Philippe Couratier et al.

Mayo Clinic Proc., vol. 66, Jan. 1991, pp. 54–82, "Motor Neuron Disease (Amyotrophic Lateral Sclerosis)", David B. Williams et al.

Rhone–Poulenc Rorer, Business News Management Decisions & Results, Apr. 4, 1995, "RILUTEK® Results of a Phase III Clinical Trial...".

Rhone–Poulenc Rorer, For Immediate Release, "Impact of Rilutek™ On Survival In Amyotrophic Lateral Sclerosis (ALS) Confirmed..." Apr. 4, 1995.

The Journal of Neuroscience, vol. 9, No. 11, Nov. 1989, pp. 3720–3737 "Riluzole, A Novel Antigultamate, Prevents Memory Loss and Hippocampal Neuronal Damage in Ischemic Gerbils", C. Malgouris, et al.

British Journal of Pharmacology, vol. 97, p. 583P, "Riluzole Antagonises Excitatory Amino Acid–Evoked Firing in Rat Facial Motoneurones in Vivo", D. Girdlestone, et al, 1987.

Therapie, vol. 45, No. 3, 1990, pp. 277–279, "Excitotoxins and Amyotrophic Lateral Sclerosis", Th. L. Munsat, et al.

Ann Neurol, vol. 22, No. 5, 1987, pp. 575–579, "Abnormal Glutamate Metabolism in Amyotrophic Lateral Sclerosis", A. Plaitakis, et al.

Neurology, vol. 41, No. 3, Supplement 1, 1991 pp. 392–393, "Dysregulation of Glutamate Metabolism in ALS: Correlation With Gender and Disease Type", A. Plaitakis, et al.

*Primary Examiner*—Marianne M. Cintins
*Assistant Examiner*—M. Moezie
*Attorney, Agent, or Firm*—Finnegan, Henderson, Farabow, Garrett & Dunner

[57] ABSTRACT

Use of 2-amino-6-(trifluoromethoxy)benzothiazole, or a salt of this compound with a pharmaceutically acceptable acid, for obtaining a medicament intended for the treatment of motor neuron diseases, in particular amyotrophic lateral sclerosis, and especially amyotrophic lateral sclerosis with early bulbar involvement or the bulbar form of the disease.

13 Claims, No Drawings

USE OF 2-AMINO-6-(TRIFLUOROMETHOXY)-BENZOTHIAZOLE FOR OBTAINING A MEDICAMENT FOR THE TREATMENT OF AMYOTROPHIC LATERAL SCLEROSIS

This is a continuation of application Ser. No. 07/945,789, filed on Sep. 16, 1992 now abandoned.

The present invention relates to the use of 2-amino-6-(trifluoromethoxy)benzothiazole, or a salt of this compound with a pharmaceutically acceptable acid, for obtaining a medicament intended for the treatment of motor neuron diseases, in particular amyotrophic lateral sclerosis commonly known as Lou Gehrig's Disease, and especially amyotrophic lateral sclerosis with early bulbar involvement or the bulbar form of the disease.

2-Amino-6-(trifluoromethoxy)benzothiazole (international non-proprietary name: riluzole) is known to be useful as an anticonvulsant, anxiolytic and hypnotic medicament (Patent EP 50,551), in the treatment of schizophrenia (EP 305,276), in the treatment of sleep disorders and depression (EP 305,277), in the treatment of cerebrovascular disorders and as an anaesthetic (EP 282,971).

It has now been found that 2-amino-6-(trifluoromethoxy)benzothiazole, or a salt of this compound with a pharmaceutically acceptable acid, is useful in the treatment of motor neuron diseases, in particular amyotrophic lateral sclerosis, and especially amyotrophic lateral sclerosis with early bulbar involvement.

This use has been determined in humans in a double-blind study against placebo: 77 patients suffering from motor neuron diseases, and in particular amyotrophic lateral sclerosis, were treated with 2×50 mg/day of riluzole orally (tablets containing a 50 mg dose) for a period of 12 to 18 months, and 78 patients received a placebo.

The results obtained are analysed in terms of survival in the study, it being understood that "study drop-outs" (departures from the study) include individuals who have actually died, and also individuals whose clinical state necessitates a tracheotomy or transfer to assisted ventilation.

In this study, 51% of patients on placebo died, whereas this percentage drops to 44% in patients on riluzole (the probability in Wilcoxon's test (R. L. PREUCTICE, Biometrika, 65, 167–179 (1978)) is equal to 0.018 and the probability in the stratified log-rank test (R. PETO and J. PETO, Journal of the Royal Statistical Society, series A, vol. 135, 185–207 (1972)) is equal to 0.06).

In subjects suffering from amyotrophic lateral sclerosis with early bulbar involvement or the bulbar form of the disease (the most serious form of the disease; the usual mean survival of this type of patient is less than 3 years), 65% of patients on placebo died, whereas this percentage drops to 47% in patients on riluzole (the probability in Wilcoxon's test is equal to 0.011 and the probability in the log-rank test (R. PETO and J. PETO, Journal of the Royal Statistical Society, series A, vol. 135, 185–207 (1972)) is equal to 0.032).

2-Amino-6-(trifluoromethoxy)benzothiazole hence increases in a statistically significant manner the survival of patients suffering from motor neuron diseases, and in particular amyotrophic lateral sclerosis, and this effect is especially marked in patients suffering from amyotrophic lateral sclerosis with early bulbar involvement or the bulbar form of the disease.

2-Amino-6-(trifluoromethoxy)benzothiazole may be prepared according to the process described in Patent EP 50,551.

As pharmaceutically acceptable salts, the addition salts with inorganic acids, such as hydrochloride, sulphate, nitrate and phosphate, or organic acids, such as acetate, propionate, succinate, oxalate, benzoate, fumarate, maleate, methanesulphonate, isethionate, theophyllineacetate, salicylate, phenolphthalinate and methylenebis(β-hydroxynaphthoate), or substitution derivatives of these derivatives, may be mentioned in particular.

The medicaments according to the invention consist of 2-amino-6-(trifluoromethoxy)benzothiazole, in free form or in the form of an addition salt with a pharmaceutically acceptable acid, in the pure state or in the form of a composition in which it is combined with any other pharmaceutically compatible product, which can be inert or physiologically active. The medicaments according to the invention may be employed orally, parenterally, rectally or topically.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica, under a stream of argon. These compositions may also comprise substances other than diluents, for example one or more lubricants such as magnesium stearate or talc, a colouring, a coating (dragees) or a varnish.

As liquid compositions for oral administration, pharmaceutically acceptable solutions, suspensions, emulsions, syrups or elixirs, containing inert diluents such as water, ethanol, glycerol, vegetable oils or liquid paraffin, may be used. These compositions can comprise substances other than diluents, for example wetting, sweetening, thickening, flavouring or stabilising-products.

The sterile compositions for parenteral administration can preferably be solutions, aqueous or non-aqueous, suspensions or emulsions. As a solvent or vehicle, water, propylene glycol, a polyethylene glycol, vegetable oils, especially olive oil, injectable organic esters, for example ethyl oleate, or other suitable organic solvents may be employed. These compositions can also contain adjuvants, especially wetting, isotonising, emulsifying, dispersing and stabilising agents. The sterilisation may be carried out in several ways, for example by aseptic filtration, by incorporating sterilising agents in the composition, by irradiation or by heating. They may also be prepared in the form of sterile solid compositions which can be dissolved at the time of use in sterile water or any other sterile injectable medium.

The compositions for rectal administration are suppositories or rectal capsules which contain, apart from the active product, excipients such as cocoa butter, semi-synthetic glycerides or polyethylene glycols.

The compositions for topical administration can be, for example, creams, lotions, mouthwashes, nasal drops or aerosols.

The doses depend on the effect sought, on the duration of the treatment and on the administration route used; they are generally between 50 and 400 mg per day administered orally for an adult, with single doses ranging from 25 to 200 mg of active substance.

Generally speaking, the doctor will determine the appropriate dosage in accordance with the age and weight and all other factors distinctive to the subject to be treated.

The examples which follow illustrate medicaments according to the invention.

EXAMPLE A

Tablets containing a 50 mg dose of active product and having the following composition are prepared according to the usual technique:

| | |
|---|---|
| 2-Amino-6-(trifluoromethoxy)benzothiazole | 50 mg |
| Mannitol | 64 mg |
| Microcrystalline cellulose | 50 mg |
| Polyvidone, excipient | 12 mg |
| Sodium carboxymethylstarch | 16 mg |
| Talc | 4 mg |
| Magnesium stearate | 2 mg |
| Colloidal silica, anhydrous | 2 mg |
| Mixture of methylhydroxypropylcellulose, polyethylene glycol 6000 and titanium dioxide (72:3.5:24.5) | 245 mg |
| q.s. 1 finished film-coated tablet weighing | |

EXAMPLE B

Hard gelatine capsules containing a 50 mg dose of active product and having the following composition are prepared according to the usual technique:

| | |
|---|---|
| 2-Amino-6-(trifluoromethoxy)benzothiazole | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE C

An injectable solution containing 10 mg of active product and having the following composition is prepared:

| | |
|---|---|
| 2-Amino-6-(trifluoromethoxy)benzothiazole | 10 mg |
| Benzoic acid | 80 mg |
| Benzyl alcohol | 0.06 cm$^3$ |
| Sodium benzoate | 80 mg |
| Ethanol, 95% | 0.4 cm$^3$ |
| Sodium hydroxide | 24 mg |
| Propylene glycol | 1.6 cm$^3$ |
| Water q. s. | 4 cm$^3$ |

I claim:

1. A method for treating a mammal with amyotrophic lateral sclerosis, comprising the step of administering to said mammal in recognized need of said treatment an effective amount of 2-amino-6-(trifluoromethoxy)benzothiazole or a pharmaceutically acceptable salt thereof.

2. The method according to claim 1 wherein said amyotrophic lateral sclerosis is with early bulbar involvement.

3. The method according to claim 1 wherein said amyotrophic lateral sclerosis is the bulbar form.

4. The method according to claim 1, wherein said effective amount comprises 25 to 200 mg of said 2-amino-6-(trifluoromethoxy)benzothiazole or said salt thereof.

5. The method according to claim 4, wherein said effective amount comprises 50 mg.

6. The method according to claim 4, wherein said effective amount comprises 25 mg.

7. The method according to claim 1, wherein said effective amount comprises 50 to 400 mg of said 2-amino-6-(trifluoromethoxy)benzothiazole or said salt thereof.

8. The method according to claim 4, wherein said effective amount comprises 200 mg.

9. The method according to claim 1, wherein said effective amount comprises 400 mg.

10. The method according to claim 1, wherein said 2-amino-6-(trifluoromethoxy)benzothiazole or said salt thereof is administered along with a pharmaceutically acceptable carrier.

11. The method according to claim 1, wherein said 2-amino-6-(trifluoromethoxy)benzothiazole or said salt thereof is administered along with a pharmaceutically compatible product.

12. The method according to claim 4, wherein said effective amount comprises 100 mg.

13. The method according to claim 1, wherein said pharmaceutically acceptable salt is an acid addition salt.

* * * * *